United States Patent
Takano et al.

(10) Patent No.: US 7,304,185 B2
(45) Date of Patent: Dec. 4, 2007

(54) PROCESS FOR PRODUCTION OF CARBONYL COMPOUNDS

(75) Inventors: Naoyuki Takano, Ibaraki (JP); Koji Hagiya, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 63 days.

(21) Appl. No.: 10/549,310

(22) PCT Filed: Mar. 24, 2004

(86) PCT No.: PCT/JP2004/004069

§ 371 (c)(1),
(2), (4) Date: Sep. 16, 2005

(87) PCT Pub. No.: WO2004/087634

PCT Pub. Date: Oct. 14, 2004

(65) Prior Publication Data
US 2006/0089506 A1 Apr. 27, 2006

(30) Foreign Application Priority Data
Mar. 31, 2003 (JP) ............................. 2003-093752

(51) Int. Cl.
*C07C 67/313* (2006.01)
*C07C 69/757* (2006.01)
*C07D 317/54* (2006.01)

(52) U.S. Cl. ................ 568/383; 568/303; 568/338; 568/360

(58) Field of Classification Search .................. None
See application file for complete search history.

(56) References Cited

FOREIGN PATENT DOCUMENTS

WO WO-03/066566 A1 8/2003

OTHER PUBLICATIONS

Barton, Derek H.R. et al., Chemistry of pentavalent organobismuth reagents. Part IX., Cleavage reactions of α-glycols, Tetrahedron, 1986, vol. 42, No. 20, pp. 5627-5636.
Barton, Derek H.R. et al., A catalytic method for α-glycol cleavage, Journal of the Chemical Society, Chemical Communications, 1981, No. 23, pp. 1232-1233.

Primary Examiner—Johann Richter
Assistant Examiner—Yevgeny Valenrod
(74) Attorney, Agent, or Firm—Birch, Stewart, Kolasch & Birch, LLP

(57) ABSTRACT

There is provided a process for the production of carbonyl compounds, characterized by reacting a diol represented by the formula (1);

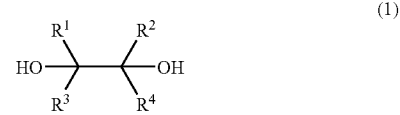

wherein $R^1$, $R^2$, $R^3$ and $R^4$ are the same or different, and independently represent a substituted or unsubstituted alkyl group, a substituted or unsubstituted aryl group, a substituted or unsubstituted aralkyl group, a substituted or unsubstituted acyl group, a substituted or unsubstituted alkoxycarbonyl group, a substituted or unsubstituted aryloxycarbonyl group, a substituted or unsubstituted aralkyloxycarbonyl group, carboxyl group or a hydrogen atom, or $R^1$ and $R^2$ or $R^3$ and $R^4$ are bonded together with the carbon atoms to which they are bonded to form a ring, provided that all of $R^1$, $R^2$, $R^3$ and $R^4$ are not hydrogen atoms simultaneously; with bromine or an inorganic bromine compound in the presence of a trivalent bismuth compound and a base to form carbonyl compounds represented by the formula (2);

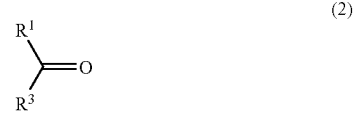

wherein $R^1$ and $R^3$ are as defined above; and the formula (3);

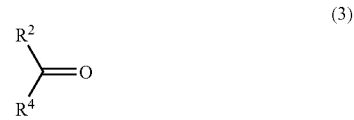

wherein $R^2$ and $R^4$ are as defined above.

11 Claims, No Drawings

PROCESS FOR PRODUCTION OF CARBONYL COMPOUNDS

TECHNICAL FIELD

The present invention relates to a process for production of carbonyl compounds.

BACKGROUND ART

Carbonyl compounds represented by aldehydes are important compounds as various chemicals and the synthetic intermediates for them. As a process for production of carbonyl compounds, a method of oxidizing vic.-diols to cleave oxidatively a carbon-carbon bond to which a hydroxyl group of the above-mentioned vic.-diols is bonded is known. For example, a method for oxidation using chromic acid (e.g. J. Am. Chem. Soc., 1962, 84, 1252), and method for oxidation using lead tetraacetate (e.g. Chem. Ber., 1931, 64, 260), method for oxidation using periodic acid or salt of periodic acid (e.g. Bull. Soc., Chim. Fr., 1928, 43, 683) and method for oxidation using a pentavalent organic bismuth agent (e.g. Tetrahedron, 1981, 37, 73) are known. However, in the method for oxidation using chromic acid, it is trouble in handling of heavy-metallic waste, and it is difficult to obtain aldehydes due to proceed oxidation reaction to give carboxylic acids. In the method for oxidation using lead tetraacetate, there is a problem of the storage stability of lead tetraacetate. In the method for oxidation using periodic acid or salt of periodic acid and method for oxidation using a pentavalent organic bismuth agent, there is a problem in that an expensive agent is required. Either of them have been not satisfactory industrially enough.

DISCLOSURE OF THE INVENTION

According to the present invention, carbonyl compounds such as aldehydes are produced more advantageously industrially from vic.-diols.

That is, the present invention provides a process for the production of carbonyl compounds, characterized by reacting a diol represented by the formula (1);

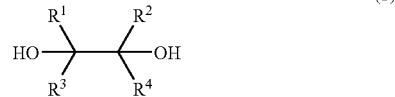

(1)

wherein $R^1$, $R^2$, $R^3$ and $R^4$ are the same or different, and independently represent a substituted or unsubstituted alkyl group, a substituted or unsubstituted aryl group, a substituted or unsubstituted aralkyl group, a substituted or unsubstituted acyl group, a substituted or unsubstituted alkoxycarbonyl group, a substituted or unsubstituted aryloxycarbonyl group, a substituted or unsubstituted aralkyloxycarbonyl group, carboxyl group or a hydrogen atom, or $R^1$ and $R^2$ or $R^3$ and $R^4$ are bonded together with the carbon atoms to which they are bonded to form a ring, provided that all of $R^1$, $R^2$, $R^3$ and $R^4$ are not hydrogen atoms simultaneously; with bromine or an inorganic bromine compound in the presence of a trivalent bismuth compound and a base to form carbonyl compounds represented by the formula (2);

(2)

wherein $R^1$ and $R^3$ are as defined above; and the formula (3);

(3)

wherein $R^2$ and $R^4$ are as defined above.

BEST MODE FOR CARRYING OUT THE INVENTION

The present invention will be illustrated in detail below.

A description will be made to $R^1$, $R^2$, $R^3$ and $R^4$ in the diol represented by the formula (1) (hereinafter simply referred to as the diol (1)) below.

Examples of the unsubstituted alkyl group include, for example, the linear, branched or cyclic alkyl group having 1 to 20 carbon atoms such as a methyl, ethyl, n-propyl, isopropyl, n-butyl, isobutyl, sec-butyl, tert-butyl, n-pentyl, hexyl, heptyl, octyl, nonyl, n-decyl, n-undecyl, n-dodecyl, n-tridecyl, n-tetradecyl, n-pentadecyl, n-hexadecyl, n-octadecyl, n-nonadecyl, n-icocyl, cyclopropyl, 2,2-dimethylcyclopropyl, cyclopentyl, cyclohexyl group and menthyl group.

Examples of the substituted alkyl group include alkyl groups which are the above-mentioned alkyl groups substituted with a) an alkoxy group (e.g. a C1-4 alkoxy group such as a methoxy, ethoxy, n-propoxy, tert-butoxy group); b) an aryloxy group such as a phenoxy and naphthyloxy group; c) an aralkyloxy group such as a benzyloxy and naphthylmethoxy group; d) an alkoxycarbonyl group such as methoxycarbonyl and ethoxycarbonyl group; e) an aryloxycarbonyl group such as a phenoxycarbonyl group; f) an aralkyloxycarbonyl group such as a benzyloxycarbonyl group; g) a halogen atom such as a fluorine, chlorine and bromine atom; h) for example, a hydroxycarbonyl group; i) for example, an alkyl group substituted with a diol group protected by isopropylidation. Specific examples of the alkyl group substituted with thus substituent include, for example, a methoxymethyl, ethoxymethyl, methoxyethyl, methoxycarbonylmethyl, 1-ethoxycarbonyl-2,2-dimethyl-3-cyclopuropyl, 7-carboxyheptyl, phenoxymethyl, 4-chlorophenoxymethyl and benzyloxymethyl group.

Examples of the unsubstituted aryl group include, for example, a phenyl and naphthyl group. Examples of the substituted aryl group include aryl groups substituted with a) the above-mentioned substituted or unsubstituted alkyl group, b) an aryl group such as a phenyl and naphthyl group, c) the above-mentioned alkoxyl group, d) an aralkyl group such as a benzyl and naphthyl group, e) the above-mentioned aryloxy group, f) the above-mentioned aralkyloxy group, g) an aryl group which includes a phenyl group substituted with a substituent such as the above-mentioned halogen atom or h) methylenedioxy group. Specific examples thereof include, for example, a 2-methylphenyl, 4-chlorophenyl, 4-methylphenyl, 4-methoxyphenyl, 3,4-methylenedioxyphenyl and 3-phenoxyphenyl group.

As the substituted or unsubstituted aralkyl group, an alkyl group substituted with the above-mentioned substituted or unsubstituted aryl group (for example, a linear, branched or cyclic alkyl group having 1 to 20 carbon atoms as the above, preferably a methyl or ethyl group) is exemplified. Specific examples thereof include, for example, a benzyl, 4-chlorobenzyl, 4-methylbenzyl, 4-methoxybenzyl, 3-phenoxybenzyl, 2,3,5,6-tetrafluorobenzyl, 2,3,5,6-tetrafluoro-4-methylbenzyl, 2,3,5,6-tetrafluoro-4-methoxybenzyl and 2,3,5,6-tetrafluoro-4-methoxymethylbenzyl group.

Examples of the substituted or unsubstituted acyl group include those which are composed of carbonyl groups and the above-mentioned substituted or unsubstituted alkyl, aryl or aralkyl groups, such as an acetyl, ethylcarbonyl, benzoyl and benzylcarbonyl group.

Examples of the substituted or unsubstituted alkoxycarboxy, aryloxycarbonyl and aralkyloxycarbonyl group include those which are composed of —O—(CO) group and the above-mentioned substituted or unsubstituted alkyl, aryl or aralkyl groups, such as a methoxycarbonyl, ethoxycarbonyl, phenoxycarbonyl and benzyloxycarbonyl group.

Examples of the ring formed by bonding $R^1$ and $R^2$ or $R^3$ and $R^4$ together with the carbon atoms to which they are bonded include, for example, a substituted or unsubstituted cycloalkyl group (for example, a cycloalkyl group having 3 to 6 carbon atoms or a cycloalkenyl group having 5 to 6 carbon atoms which may be branched, and a cycloalkyl group having 3 to 6 carbon atoms, cycloalkyl group, or cycloalkenyl group having 5 to 6 carbon atoms which may be branched and are substituted with a substituent exemplified as the substituent of the above-mentioned substituted alkyl group such as a cyclopropane ring, a dimethylcyclopropane ring, a cyclobutane ring, a cyclopentane ring, a cyclohexane ring, a cyclopentene ring and a cyclohexene ring).

Examples of the diol (1) include, for example, pinacol, 2,3-butanediol, 1,2-cyclohexanediol, 1,2-cyclooctanediol, 1-methyl-1,2-cyclohexanediol, cyclohexene-1,2-diol, 1,2-indanediol, 1,2-diphenyl-1,2-ethanediol, 1,2:5,6-di-O-isopropylidene-mannitol, decalin-9,10-diol, 1,2-(methylenedioxy)-4-(propane-1,2-diol)benzene, 6,6-dimethyl-bicyclo[3.1.1]heptane-2,3-diol, 3,7,7-trimethyl-bicyclo[4.1.0]heptane-3,4-diol, 9,10-dihydroxyoctadecanoic acid, N,N,N,N-tetramethyl-L-tartardiamide, and 1,1'-(2,3-dihydroxy-1,4-dioxo-1,4-butanediyl)bis-pyrrolidine.

As the diol (1), a commercially available compound or a compound produced according to the known methods such as a method for reacting a corresponding epoxy compound with an alkali may be used.

When the diol (1) has an asymmetric carbon atom within the molecule, the diol (1) has optically isomers and any one optical isomer thereof or a mixture thereof may be used in the present invention.

Examples of the trivalent bismuth compound include, for example, triarylbismuth compounds such as triphenylbismuth, tri(2-methoxyphenyl)bismuth, tri(4-methoxyphenyl)bismuth, trimesytylbismuth, and tri(4-fluorophenyl)bismuth, diarylalkylbismuth compounds such as diphenylmethylbismuth, trivalent bismuth halide compounds such as bismuth trichloride, preferably triarylbismuth compound. The amount of the bismuth compound used may be catalytic amount per 1 mole of the diol (1), and it is usually 0.001 to 1 mole, preferably about 0.005 to 0.05 mole per 1 mole of the diol (1).

Examples of the base include, for example, alkali metal carbonates such as sodium carbonate, potassium carbonate and cesium carbonate, and alkali metal hydroxides such as lithium hydroxide, sodium hydroxide and potassium hydroxide, preferably alkali metal carbonate, especially preferably potassium carbonate. The amount of the base used is usually 1 mole or more per 1 mole of the diol (1), and there is no specific upper limit, and it is usually 10 moles or less per 1 mole of the diol (1).

Examples of the inorganic bromine compound include, for example, bromine chloride and phosphorus tribromide. The amount of bromine or the inorganic bromine compound used is usually 1 mole or more per 1 mole of the diol (1), and there is no specific upper limit and it is usually 3 mole or less per 1 mole of the diol (1). Bromine or the inorganic bromine compound is used as it is or in the form of a solution obtained by dissolving with a solvent described below. Two or more kinds of bromine or the inorganic bromine compound may be added simultaneously, and the sum of the amount of each bromine or inorganic compound may be in a range of the above-mentioned amount.

The present reaction may be carried out without using a solvent and preferably the reaction is carried out in the presence of a solvent. The solvent is not particularly limited in so far as it is inactive against the reaction and the diol (1) can dissolve in it. Examples of the solvent include, for example, water; alcohol solvents such as tert-butyl alcohol; alkylnitrile solvents such as acetonitrile and propionitrile; ether solvents such as diethyl ether, tert-butyl methyl ether and tetrahydrofuran; ester solvents such as ethyl acetate; and halogenated hydrocarbon solvents such as dichloromethane, dichloroethane, chloroform, carbon tetrachloride, chlorobenzene and dichlorobenzene. The solvent may be used alone or in the form of a mixture. The amount of the solvent used is not particularly limited.

The reaction of the present invention is preferably carried out in the presence of an amide compound having at least one hydrogen atom on the nitrogen atom, or an imide compound having at least one hydrogen atom on the nitrogen atom (hereinafter simply referred to as the amide compound or the imide compound). The carbonyl compound can be obtained in better yield by carrying out the reaction according to thus embodiment. Examples of the amide compound or the imide compound include, for example, an amide compound such as acetamide, N-methylacetamide, ethanamide, propanamide, benzamide and N-methylbenzamide; and an imide compound such as succinimide, phthalimide and 1,2-cyclohexanedicarboxyimide. The amount of the amide compound or the imide compound may be catalytic amount per 1 mole of the diol (1), and it is usually 0.01 mole or more, preferably 0.05 mole or more. There is no specific upper limit, and it is usually 1 mole or less per 1 mole of the diol (1).

The reaction temperature is usually about −10 to 100° C.

The present reaction proceeds by mixing the bismuth compound, the base, the diol (1), bromine or the inorganic bromine compound, and if necessary, the amide compound or imide compound. The mixing order is not particularly limited and usually, bromine or the inorganic bromine compound is added to the mixture of the diol (1), the bismuth compound, the base, and if necessary, the amide compound or imide compound. In the viewpoint of obtaining the desired carbonyl compound in better yield, it is preferable to mix previously a part of the diol (1), the bismuth compound, the base and if necessary, the amide compound or imide compound and add the remaining diol (1) and bromine or the inorganic bromine compound to the resulting mixture simultaneously.

The carbonyl compound represented by the formula (2) (hereinafter, simply referred to as the carbonyl compound (2)) and the carbonyl compound represented by the formula (3) (hereinafter, simply referred to as the carbonyl compound (3)) are produced by reacting the diol (1) with bromine or the inorganic bromine compound in the presence of the bismuth compound and the base. For example, the carbonyl compound (2) and the carbonyl compound (3) can be isolated by concentrating the obtained reaction mixture as it is or after filtering insolubles, if necessary. Alternatively, the carbonyl compound (2) and the carbonyl compound (3) can be also isolated by adding, if necessary, water and/or a water-insoluble solvent to the reaction mixture, then extracting and subsequently concentrating the obtained organic layer. The isolated carbonyl compound (2) and carbonyl compound (3) may be separated or purified by means such as distillation and/or column chromatography. It is preferable to neutralize the reaction mixture before concentration in order to prevent the carbonyl compound (2) and the carbonyl compound (3) from decomposing or condensing while concentrating.

Examples of the obtained carbonyl compound (2) and carbonyl compound (3) include, for example, acetone, acetaldehyde, glutaraldehyde, adipoaldehyde, 5-acetyl-1-pentanal, benzaldehyde, 2,3-O-isopropylidene-glyceraldehyde, 1,6-cyclodecanedione, heliotropin, 3-formyl-2,2-dimethyl-cyclobutanacetaldehyde, 2,2-dimethyl-(3-oxopropyl)cyclopropanecarbaldehyde, nonylaldehyde, 9-oxononanonic acid, N,N-dimethylglyoxylamide and N-glyoxyloylpyrrolidine.

Next, an application of the present invention will be illustrated by a specific example.

When a compound represented by the formula (4)

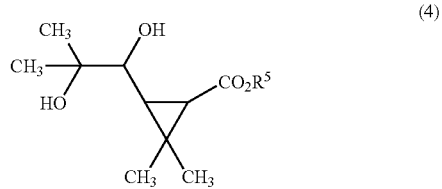

(4)

wherein $R^5$ represents a substituted or unsubstituted alkyl group, a substituted or unsubstituted aryl group or a substituted or unsubstituted aralkyl group (hereinafter, simply referred to as the diol (4)), is used as the diol (1) in the present reaction, an aldehyde represented by the formula (5)

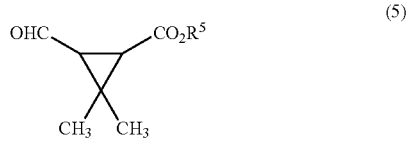

(5)

wherein $R^5$ are as defined above (hereinafter, simply referred to as the aldehyde (5)) can be obtained as the carbonyl compound.

The substituted or unsubstituted alkyl group, the substituted or unsubstituted aryl group and the substituted or unsubstituted aralkyl group include the same groups as described above.

$R^5$ represents preferably a linear, branched or cyclic alkyl group having 1 to 20 carbon atoms as the above, or an aralkyl group which may be substituted with at least one substituent selected from a) a halogen atom, b) an alkyl group such as a methyl and ethyl group, c) an alkoxy group such as a methoxy group, d) an alkoxyalkyl group such as a methoxymethyl group, and e) an aryloxy group such as a phenoxy group (e.g. a benzyl group).

Examples of the diol (4) include, for example, methyl 3,3-dimethyl-2-(2-methyl-1,2-dihydroxypropyl)cyclopropanecarboxylate, ethyl 3,3-dimethyl-2-(2-methyl-1,2-dihydroxypropyl)cyclopropanecarboxylate, isopropyl 3,3-dimethyl-2-(2-methyl-1,2-dihydroxypropyl)cyclopropanecarboxylate, tert-butyl 3,3-dimethyl-2-(2-methyl-1,2-dihydroxypropyl)cyclopropanecarboxylate, cyclohexyl 3,3-dimethyl-2-(2-methyl-1,2-dihydroxypropyl)cyclopropanecarboxylate, menthyl 3,3-dimethyl-2-(2-methyl-1,2-dihydroxypropyl)cyclopropanecarboxylate, benzyl 3,3-dimethyl-2-(2-methyl-1,2-dihydroxypropyl)cyclopropanecarboxylate, 4-chlorobenzyl 3,3-dimethyl-2-(2-methyl-1,2-dihydroxypropyl)cyclopropanecarboxylate, 2,3,5,6-tetrafluorobenzyl 3,3-dimethyl-2-(2-methyl-1,2-dihydroxypropyl)cyclopropanecarboxylate, 2,3,5,6-tetrafluoro-4-methylbenzyl 3,3-dimethyl-2-(2-methyl-1,2-dihydroxypropyl)cyclopropanecarboxylate, 2,3,5,6-tetrafluoro-4-methoxybenzyl 3,3-dimethyl-2-(2-methyl-1,2-dihydroxypropyl)cyclopropanecarboxylate, 2,3,5,6-tetrafluoro-4-methoxymethylbenzyl 3,3-dimethyl-2-(2-methyl-1,2-dihydroxypropyl)cyclopropanecarboxylate, and 3-phenoxybenzyl 3,3-dimethyl-2-(2-methyl-1,2-dihydroxypropyl)cyclopropanecarboxylate.

Thus diol (4) has a cis-isomer having the group shown by —CO$_2$R and 2-methyl-1,2-dihydroxypropyl group on the same side with respect to the cyclopropane ring plane and a trans-isomer having the groups on the opposite side, and any one of the cis-isomer and the trans-isomer or a mixture thereof may be used in the present invention. When the mixture of the cis-isomer and the trans-isomer is used, the mixing ratio thereof is not limited particularly.

Thus diol (4) has optically isomers due to having asymmetric carbon atoms within the molecule and any one optical isomer thereof or a mixture thereof may be used in the present invention.

The diol (4) can be produced according to the known method such as a method which is that the corresponding chrysamthemic acid ester is subjected to the oxidation treatment with hydrogen peroxide in the presence of a tungsten catalyst and then conducting reduction treatment (e.g. EP-1188735).

Examples of the obtained aldehyde (5) include, for example, methyl 3,3-dimethyl-2-formylcyclopropanecarboxylate, ethyl 3,3-dimethyl-2-formylcyclopropanecarboxylate, isopropyl 3,3-dimethyl-2-formylcyclopropanecarboxylate, tert-butyl 3,3-dimethyl-2-formylcyclopropanecarboxylate, cyclohexyl 3,3-dimethyl-2-formylcyclopropanecarboxylate, menthyl 3,3-dimethyl-2-formylcyclopropanecarboxylate, benzyl 3,3-dimethyl-2-formylcyclopropanecarboxylate, 4-chlorobenzyl 3,3-dimethyl-2-formylcyclopropanecarboxylate, 2,3,5,6-tetrafluorobenzyl 3,3-dimethyl-2-formylcyclopropanecarboxylate, 2,3,5,6-tetrafluoro-4-methylbenzyl 3,3-dimethyl-2-formylcyclopropanecarboxylate, 2,3,5,6-tetrafluoro-4-methoxybenzyl 3,3-dimethyl-2-formylcyclopropanecarboxylate, 2,3,5,6-tetrafluoro-4-methoxymethylbenzyl 3,3-dimethyl-2- formylcyclopropanecarboxylate, and 3-phenoxybenzyl 3,3-dimethyl-2-formylcyclopropanecarboxylate.

Also, when a trans-isomer is used as the diol (4), a trans-isomer of the aldehyde (5) is obtained, and when a cis-isomer is used as the diol (4), a cis-isomer of the aldehyde (5) is obtained. When an optically active diol (4) is used, optically active aldehyde (5) is obtained As above, the present reaction can be applied to the industrial process for production of the aldehyde (5) which is an important compound as the synthetic intermediates of pyrethroid household agents for epidemic prevention and insecticides.

EXAMPLE

The present invention is illustrated below in more detail with Examples, but it is not limited thereto. The analysis was conducted with gas chromatography internal standard method.

Example 1

Into a 100 mL four-neck flask equipped with a stirrer and a reflux condenser, 0.2 g of methyl trans-3,3-dimethyl-2-(1,2-dihydroxy-2-methylpropyl)cyclopropanecarboxylate (content: 94.1 wt %), 30 mL of acetonitrile, 0.1 g of triphenylbismuth and 13.1 g of potassium carbonate were charged. 10 mL of acetonitrile solution in which 2 g of methyl trans-3,3-dimethyl-2-(1,2-dihydroxy-2-methylpropyl)cyclopropanecarboxylate (content: 94.1 wt %) was dissolved, and 10 mL of acetonitrile solution in which 1.7 g of bromine was dissolved were added dropwise simultaneously thereto at 40° C. over 4 hrs. The reaction mixture was stirred for 30 minutes to effect reaction at the same temperature and then insoluble matter was removed from the reaction mixture by filtration, and the removed insoluble matter was washed with about 25 mL of acetonitrile, and 62.1 g of an organic phase containing methyl trans-3,3-dimethyl-2-formylcyclopropanecarboxylate was obtained.

Content of methyl trans-3,3-dimethyl-2-formylcyclopropanecarboxylate: 2.1 wt %.

Yield: 88%.

Example 2

Into a 100 mL four-neck flask equipped with a stirrer and a reflux condenser, 2.2 g of methyl trans-3,3-dimethyl-2-(1,2-dihydroxy-2-methylpropyl)cyclopropanecarboxylate (content: 94.1 wt %), 30 mL of acetonitrile (water content 3 wt %), 0.05 g of triphenylbismuth, 0.1 g of succinimide and 5.3 g of potassium carbonate were charged. 20 mL of acetonitrile solution in which 1.9 g of bromine was dissolved was added dropwise thereto over 3.8 hrs. The reaction mixture was stirred for 30 minutes to effect reaction at the same temperature and then insoluble matter was removed from the reaction mixture by filtration, and the removed insoluble matter was washed with about 25 mL of acetonitrile, and 60.6 g of an organic phase containing methyl trans-3,3-dimethyl-2-formylcyclopropanecarboxylate was obtained.

Content of methyl trans-3,3-dimethyl-2-formylcyclopropanecarboxylate: 2.1 wt %.

Yield: 86%.

Example 3

Into a 100 mL four-neck flask equipped with a stirrer and a reflux condenser, 0.22 g of methyl trans-3,3-dimethyl-2-(1,2-dihydroxy-2-methylpropyl)cyclopropanecarboxylate (content: 94 wt %), 20 mL of acetonitrile (water content 3 wt %), 0.1 g of succinimide, 0.05 g of triphenylbismuth and 5.3 g of potassium carbonate were charged. 10 mL of acetonitrile (water content 3 wt %) solution in which 1.98 g of methyl trans-3,3-dimethyl-2-(1,2-dihydroxy-2-methylpropyl)cyclopropanecarboxylate (content: 94 wt %) was dissolved, and 20 mL of acetonitrile (water content 3 wt %) solution in which 1.9 g of bromine was dissolved were added dropwise thereto through parallel at an inner temperature of 40° C. over 3 hrs and 3.8 hrs, respectively. The reaction mixture was stirred for 30 minutes to effect reaction at the same temperature and then insoluble matter was removed from the reaction mixture by filtration, and the removed insoluble matter was washed with about 25 mL of acetonitrile, and 59.4 g of an organic phase containing methyl trans-3,3-dimethyl-2-formylcyclopropanecarboxylate was obtained.

Content of methyl trans-3,3-dimethyl-2-formylcyclopropanecarboxylate: 2.4 wt %.

Yield: 97%.

Example 4

Into a 100 mL four-neck flask equipped with a stirrer and a reflux condenser, 0.10 g of 1,2-(methylenedioxy)-4-(propane-1,2-diol)benzene (content: 91 wt %), 10 mL of acetonitrile (water content 3 wt %), 0.05 g of succinimide, 0.05 g of triphenylbismuth and 2.7 g of potassium carbonate were charged. 10 mL of acetonitrile (water content 3 wt %) solution in which 0.88 g of 1,2-(methylenedioxy)-4-(propane-1,2-diol)benzene (content: 91 wt %) was dissolved, and 10 mL of acetonitrile (water content 3 wt %) solution in which 0.94 g of bromine was dissolved were added dropwise thereto through parallel at an inner temperature of 55° C. over 3 hrs and 3.8 hrs, respectively. The reaction mixture was stirred for 30 minutes to effect reaction at the same temperature and then insoluble matter was removed from the reaction mixture by filtration, and the removed insoluble matter was washed with about 15 mL of acetonitrile, and 34.1 g of an organic phase containing heliotropin was obtained.

Content of heliotropin: 1.8 wt %.

Yield: 91%.

INDUSTRIAL APPLICABILITY

According to the method of the present invention, carbonyl compounds can be produced from vic-diols using inexpensive bromine and therefore it is advantageous industrially.

What is claimed is:

1. A process for the production of carbonyl compounds, characterized by reacting a diol represented by the formula (1);

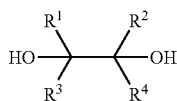

wherein $R^1$, $R^2$, $R^3$ and $R^4$ are the same or different, and independently represent a substituted or unsubstituted alkyl group, a substituted or unsubstituted aryl group, a substituted or unsubstituted aralkyl group, a substituted or unsubstituted acyl group, a substituted or unsubstituted alkoxycarbonyl group, a substituted or unsubstituted aryloxycarbonyl group, a substituted or unsubstituted aralkyloxycarbonyl group, carboxyl group or a hydrogen atom, or $R^1$ and $R^2$ or $R^3$ and $R^4$ are bonded together with the carbon atoms to which they are bonded to form a ring, provided that all of $R^1$, $R^2$, $R^3$ and $R^4$ are not hydrogen atoms simultaneously; with bromine or an inorganic bromine compound in the presence of a trivalent bismuth compound and a base, wherein the base is an alkali metal carbonate or alkali metal hydroxide, to form carbonyl compounds represented by the formula (2):

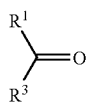

wherein $R^1$ and $R^3$ are as defined above; and the formula (3):

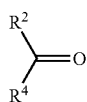

wherein $R^2$ and $R^4$ are as defined above, and mixing previously a portion of the diol represented by the formula (1), the bismuth compound and the base, and adding the remaining diol represented by the formula (1) and bromine or the inorganic bromine compound to the resulting mixture simultaneously.

2. A process according to claim 1, wherein the trivalent bismuth compound is a triarylbismuth compound.

3. A process according to claim 1, which is characterized in carrying out the reaction in the presence of an amide compound having at least one hydrogen atom on the nitrogen atom, or an imide compound having at least one hydrogen atom on the nitrogen atom.

4. A process according to claim 3, which is characterized in mixing previously a part of the diol represented by the formula (1), the bismuth compound, the base, and the amide compound having at least one hydrogen atom on the nitrogen atom or the imide compound having at least one hydrogen atom on the nitrogen atom, and adding the remaining diol represented by the formula (1) and bromine or the inorganic bromine compound to the resulting mixture simultaneously.

5. A process according to claim 2, wherein the triarylbismuth compound is triphenylbismuth, tri(2-methoxyphenyl)bismuth, tri(4-methoxyphenyl)bismuth, trimesitylbismuth or tri(4-fluorophenyl)bismuth.

6. A process according to claim 3, wherein the amide compound having at least one hydrogen atom on the nitrogen atom, or the imide compound having at least one hydrogen atom on the nitrogen atom is acetamide, N-methylacetamide, ethanamide, propanamide, benzamide, N-methylbenzamide, succinimide, phthalimide, or 1,2-cyclohexanedicarboxyimide.

7. A process according to claim 1, wherein the inorganic bromine compound is bromine chloride or phosphorus tribromide.

8. A process according to claim 1, wherein the base is potassium carbonate.

9. A process according to claim 1, wherein the diol represented by the formula (1) is a compound represented by the formula (4)

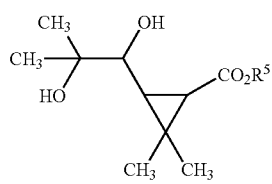

wherein $R^5$ represents a substituted or unsubstituted alkyl group, a substituted or unsubstituted aryl group or a substituted or unsubstituted aralkyl group.

10. A process according to claim 9, wherein $R^5$ is i) a linear, branched or cyclic alkyl group having 1 to 20 carbon atoms, or ii) an aralkyl group which may be substituted with at least one group selected from a) a halogen atom, b) an alkyl group, c) an alkoxy group, d) an alkoxyalkyl group and e) an aryloxy group.

11. A process according to claim 9, wherein $R^5$ is i) a methyl group, or ii) a benzyl group which may be substituted with at least one group selected from a) a halogen atom, b) a methyl group, c) a methoxy group, d) a methoxymethyl group and e) phenoxy group.

* * * * *